United States Patent
Vind et al.

(10) Patent No.: US 9,963,690 B2
(45) Date of Patent: May 8, 2018

(54) GLUCOAMYLASE VARIANTS AND POLYNUCLEOTIDES ENCODING SAME

(71) Applicant: NOVOZYMES A/S, Bagsvaerd (DK)

(72) Inventors: Jesper Vind, Vaerloese (DK); Santhosh Mepadam Vasu, Bangalore (IN); Rakhi Saikia, Bangalore (IN); Aditya Basu, Bangalore (IN)

(73) Assignee: NOVOZYMES A/S, Bagsvaerd (DK)

( * ) Notice: Subject to any disclaimer, the term of this patent is extended or adjusted under 35 U.S.C. 154(b) by 0 days. days.

(21) Appl. No.: 14/787,422

(22) PCT Filed: Apr. 29, 2014

(86) PCT No.: PCT/EP2014/058686
§ 371 (c)(1),
(2) Date: Oct. 27, 2015

(87) PCT Pub. No.: WO2014/177541
PCT Pub. Date: Nov. 6, 2014

(65) Prior Publication Data
US 2016/0145592 A1    May 26, 2016

(30) Foreign Application Priority Data
Apr. 30, 2013   (IN) ............................ 1933/CHE/2013

(51) Int. Cl.
*C12P 7/06*  (2006.01)
*C12N 9/34*  (2006.01)
*C12N 9/26*  (2006.01)
*C12P 19/02*  (2006.01)
*C12P 19/20*  (2006.01)

(52) U.S. Cl.
CPC ......... *C12N 9/2428* (2013.01); *C12N 9/2408* (2013.01); *C12P 19/02* (2013.01); *C12P 19/20* (2013.01); *C12Y 302/01003* (2013.01)

(58) Field of Classification Search
CPC ...................... C12N 9/2428; C12Y 302/01003
USPC .................................................. 435/161, 205
See application file for complete search history.

(56) References Cited

U.S. PATENT DOCUMENTS 9,127,262 B2 *   9/2015   Landvik ............... C12N 9/2428

FOREIGN PATENT DOCUMENTS

WO    2006/069289 A2    6/2006
WO    2011/068803 A1    6/2011

* cited by examiner

*Primary Examiner* — Tekchand Saidha
(74) *Attorney, Agent, or Firm* — David Fazzolare

(57) ABSTRACT

The present invention relates to glucoamylase variants. The present invention also relates to polynucleotides encoding the variants; nucleic acid constructs, vectors, and host cells comprising the polynucleotides; and methods of using the variants.

20 Claims, No Drawings

SEQUENCE LISTING

<160> NUMBER OF SEQ ID NOS: 3

<210> SEQ ID NO 1
<211> LENGTH: 1725
<212> TYPE: DNA
<213> ORGANISM: Artificial Sequence
<220> FEATURE:
<223> OTHER INFORMATION: Synthentic gene

<400> SEQUENCE: 1

| | | | | | |
|---|---|---|---|---|---|
| atgcgtttca | cgctcctcac | ctccctcctg | ggcctcgccc | tcggcgcgtt | cgcgcagtcg | 60 |
| agtgcggccg | acgcgtacgt | cgcgtccgaa | tcgcccatcg | ccaaggcggg | tgtgctcgcc | 120 |
| aacatcgggc | ccagcggctc | caagtccaac | ggagcaaagg | caggcatcgt | gattgcaagt | 180 |
| ccgagcacat | ccaacccgaa | ctacctgtac | acatggacgc | gcgactcgtc | cctcgtgttc | 240 |
| aaggcgctca | tcgaccagtt | caccactggc | gaagatacct | cgctccgaac | tctgattgac | 300 |
| gagttcacct | cggcggaggc | catactccag | caggtgccga | acccgagcgg | gacagtcagc | 360 |
| actggaggcc | tcggcgagcc | caagttcaac | atcgacgaga | ccgcgttcac | ggatgcctgg | 420 |
| ggtcgtcctc | agcgcgatgg | tcccgctctc | cgggcgactg | ccatcatcac | ctacgccaac | 480 |
| tggctcctcg | acaacaagaa | cacgacctac | gtgaccaaca | ctctctggcc | tatcatcaag | 540 |
| ctcgacctcg | actacgtcgc | cagcaactgg | aaccagtcca | cgtttgatct | ctgggaggag | 600 |
| attaactcct | cgtcgttctt | cactaccgcc | gtccagcacc | gtgctctgcg | cgagggcgcg | 660 |
| actttcgcta | tcgcatcgg | acaaacctcg | gtggtcagcg | ggtacaccac | ccaagcaaac | 720 |
| aaccttctct | gcttcctgca | gtcgtactgg | aaccccaccg | gcggctatat | caccgcaaac | 780 |
| acgggcggcg | gccgctctgg | caaggacgcg | aacaccgttc | tcacgtcgat | ccacaccttc | 840 |
| gacccggccg | ctggatgcga | cgctgttacg | ttccagccgt | gctcggacaa | ggcgctgtcg | 900 |
| aacttgaagg | tgtacgtcga | tgcgttccgc | tcgatctact | ccatcaacag | cgggatcgcc | 960 |
| tcgaatgcgg | ccgttgctac | cggccgctac | cccgaggaca | gctacatggg | cggaaaccca | 1020 |
| tggtacctca | ccacctccgc | cgtcgctgag | cagctctacg | atgcgctcat | tgtgtggaac | 1080 |
| aaacttggcg | ccctgaacgt | cacgagcacc | tccctcccct | tcttccagca | gttctcgtca | 1140 |
| ggcgtcaccg | tcggcaccta | tgcctcatcc | tcgtccacct | tcaagacgct | cacttccgcc | 1200 |
| atcaagacct | tcgccgacgg | cttcctcgcg | gtcaacgcca | agtacacgcc | ctcgaacggc | 1260 |
| ggccttgctg | aacagtacag | ccggagcaac | ggctcgcccg | tcagcgctgt | ggacctgacg | 1320 |
| tggagctatg | ctgctgccct | cacgtcgttt | gctgcgcgct | caggcaagac | gtatgcgagc | 1380 |
| tggggcgcgg | cgggtttgac | tgtcccgacg | acttgctcgg | ggagtggcgg | tgctgggact | 1440 |
| gtggccgtca | ccttcaacgt | gcaggcgacc | accgtgttcg | gcgagaacat | ttacatcaca | 1500 |
| ggctcggtcc | ccgctctcca | gaactggtcg | cccgacaacg | cgctcatcct | ctcagcggcc | 1560 |
| aactacccca | cttggagcat | caccgtgaac | ctgccggcga | gcacgacgat | cgagtacaag | 1620 |
| tacattcgca | agttcaacgg | cgcggtcacc | tgggagtccg | acccgaacaa | ctcgatcacg | 1680 |
| acgcccgcga | gcggcacgtt | cacccagaac | gacacctggc | ggtag | | 1725 |

<210> SEQ ID NO 2
<211> LENGTH: 574
<212> TYPE: PRT
<213> ORGANISM: Trametes cingulata

<400> SEQUENCE: 2

Met Arg Phe Thr Leu Leu Thr Ser Leu Leu Gly Leu Ala Leu Gly Ala

-continued

```
1               5                   10                  15
Phe Ala Gln Ser Ser Ala Ala Asp Ala Tyr Val Ala Ser Glu Ser Pro
                20                  25                  30

Ile Ala Lys Ala Gly Val Leu Ala Asn Ile Gly Pro Ser Gly Ser Lys
                35                  40                  45

Ser Asn Gly Ala Lys Ala Gly Ile Val Ile Ala Ser Pro Ser Thr Ser
 50                  55                  60

Asn Pro Asn Tyr Leu Tyr Thr Trp Thr Arg Asp Ser Ser Leu Val Phe
 65                  70                  75                  80

Lys Ala Leu Ile Asp Gln Phe Thr Thr Gly Glu Asp Thr Ser Leu Arg
                85                  90                  95

Thr Leu Ile Asp Glu Phe Thr Ser Ala Glu Ala Ile Leu Gln Gln Val
                100                 105                 110

Pro Asn Pro Ser Gly Thr Val Ser Thr Gly Gly Leu Gly Glu Pro Lys
                115                 120                 125

Phe Asn Ile Asp Glu Thr Ala Phe Thr Asp Ala Trp Gly Arg Pro Gln
 130                 135                 140

Arg Asp Gly Pro Ala Leu Arg Ala Thr Ala Ile Ile Thr Tyr Ala Asn
 145                 150                 155                 160

Trp Leu Leu Asp Asn Lys Asn Thr Thr Tyr Val Thr Asn Thr Leu Trp
                165                 170                 175

Pro Ile Ile Lys Leu Asp Leu Asp Tyr Val Ala Ser Asn Trp Asn Gln
                180                 185                 190

Ser Thr Phe Asp Leu Trp Glu Glu Ile Asn Ser Ser Phe Phe Thr
                195                 200                 205

Thr Ala Val Gln His Arg Ala Leu Arg Glu Gly Ala Thr Phe Ala Asn
 210                 215                 220

Arg Ile Gly Gln Thr Ser Val Val Ser Gly Tyr Thr Thr Gln Ala Asn
 225                 230                 235                 240

Asn Leu Leu Cys Phe Leu Gln Ser Tyr Trp Asn Pro Thr Gly Gly Tyr
                245                 250                 255

Ile Thr Ala Asn Thr Gly Gly Arg Ser Gly Lys Asp Ala Asn Thr
                260                 265                 270

Val Leu Thr Ser Ile His Thr Phe Asp Pro Ala Ala Gly Cys Asp Ala
                275                 280                 285

Val Thr Phe Gln Pro Cys Ser Asp Lys Ala Leu Ser Asn Leu Lys Val
                290                 295                 300

Tyr Val Asp Ala Phe Arg Ser Ile Tyr Ser Ile Asn Ser Gly Ile Ala
 305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
                340                 345                 350

Tyr Asp Ala Leu Ile Val Trp Asn Lys Leu Gly Ala Leu Asn Val Thr
                355                 360                 365

Ser Thr Ser Leu Pro Phe Phe Gln Gln Phe Ser Ser Gly Val Thr Val
                370                 375                 380

Gly Thr Tyr Ala Ser Ser Ser Ser Thr Phe Lys Thr Leu Thr Ser Ala
 385                 390                 395                 400

Ile Lys Thr Phe Ala Asp Gly Phe Leu Ala Val Asn Ala Lys Tyr Thr
                405                 410                 415

Pro Ser Asn Gly Gly Leu Ala Glu Gln Tyr Ser Arg Ser Asn Gly Ser
                420                 425                 430
```

-continued

```
Pro Val Ser Ala Val Asp Leu Thr Trp Ser Tyr Ala Ala Ala Leu Thr
            435                 440                 445

Ser Phe Ala Ala Arg Ser Gly Lys Thr Tyr Ala Ser Trp Gly Ala Ala
450                 455                 460

Gly Leu Thr Val Pro Thr Thr Cys Ser Gly Ser Gly Gly Ala Gly Thr
465                 470                 475                 480

Val Ala Val Thr Phe Asn Val Gln Ala Thr Thr Val Phe Gly Glu Asn
            485                 490                 495

Ile Tyr Ile Thr Gly Ser Val Pro Ala Leu Gln Asn Trp Ser Pro Asp
                500                 505                 510

Asn Ala Leu Ile Leu Ser Ala Ala Asn Tyr Pro Thr Trp Ser Ile Thr
            515                 520                 525

Val Asn Leu Pro Ala Ser Thr Thr Ile Glu Tyr Lys Tyr Ile Arg Lys
530                 535                 540

Phe Asn Gly Ala Val Thr Trp Glu Ser Asp Pro Asn Asn Ser Ile Thr
545                 550                 555                 560

Thr Pro Ala Ser Gly Thr Phe Thr Gln Asn Asp Thr Trp Arg
                565                 570

<210> SEQ ID NO 3
<211> LENGTH: 556
<212> TYPE: PRT
<213> ORGANISM: Trametes cingulata

<400> SEQUENCE: 3

Gln Ser Ser Ala Ala Asp Ala Tyr Val Ala Ser Glu Ser Pro Ile Ala
1               5                   10                  15

Lys Ala Gly Val Leu Ala Asn Ile Gly Pro Ser Gly Ser Lys Ser Asn
            20                  25                  30

Gly Ala Lys Ala Gly Ile Val Ile Ala Ser Pro Ser Thr Ser Asn Pro
        35                  40                  45

Asn Tyr Leu Tyr Thr Trp Thr Arg Asp Ser Ser Leu Val Phe Lys Ala
50                  55                  60

Leu Ile Asp Gln Phe Thr Thr Gly Glu Asp Thr Ser Leu Arg Thr Leu
65                  70                  75                  80

Ile Asp Glu Phe Thr Ser Ala Glu Ala Ile Leu Gln Gln Val Pro Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Asp Ala Trp Gly Arg Pro Gln Arg Asp
        115                 120                 125

Gly Pro Ala Leu Arg Ala Thr Ala Ile Ile Thr Tyr Ala Asn Trp Leu
130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Ser Phe Phe Thr Thr Ala
            180                 185                 190

Val Gln His Arg Ala Leu Arg Glu Gly Ala Thr Phe Ala Asn Arg Ile
        195                 200                 205

Gly Gln Thr Ser Val Val Ser Gly Tyr Thr Thr Gln Ala Asn Asn Leu
210                 215                 220

Leu Cys Phe Leu Gln Ser Tyr Trp Asn Pro Thr Gly Gly Tyr Ile Thr
```

-continued

```
                225                 230                 235                 240
Ala Asn Thr Gly Gly Gly Arg Ser Gly Lys Asp Ala Asn Thr Val Leu
                    245                 250                 255

Thr Ser Ile His Thr Phe Asp Pro Ala Ala Gly Cys Asp Ala Val Thr
                    260                 265                 270

Phe Gln Pro Cys Ser Asp Lys Ala Leu Ser Asn Leu Lys Val Tyr Val
                275                 280                 285

Asp Ala Phe Arg Ser Ile Tyr Ser Ile Asn Ser Gly Ile Ala Ser Asn
                290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                    325                 330                 335

Ala Leu Ile Val Trp Asn Lys Leu Gly Ala Leu Asn Val Thr Ser Thr
                    340                 345                 350

Ser Leu Pro Phe Phe Gln Gln Phe Ser Ser Gly Val Thr Val Gly Thr
                    355                 360                 365

Tyr Ala Ser Ser Ser Thr Phe Lys Thr Leu Thr Ser Ala Ile Lys
                370                 375                 380

Thr Phe Ala Asp Gly Phe Leu Ala Val Asn Ala Lys Tyr Thr Pro Ser
385                 390                 395                 400

Asn Gly Gly Leu Ala Glu Gln Tyr Ser Arg Ser Asn Gly Ser Pro Val
                    405                 410                 415

Ser Ala Val Asp Leu Thr Trp Ser Tyr Ala Ala Leu Thr Ser Phe
                    420                 425                 430

Ala Ala Arg Ser Gly Lys Thr Tyr Ala Ser Trp Gly Ala Ala Gly Leu
                435                 440                 445

Thr Val Pro Thr Thr Cys Ser Gly Ser Gly Gly Ala Gly Thr Val Ala
                    450                 455                 460

Val Thr Phe Asn Val Gln Ala Thr Thr Val Phe Gly Glu Asn Ile Tyr
465                 470                 475                 480

Ile Thr Gly Ser Val Pro Ala Leu Gln Asn Trp Ser Pro Asp Asn Ala
                    485                 490                 495

Leu Ile Leu Ser Ala Ala Asn Tyr Pro Thr Trp Ser Ile Thr Val Asn
                500                 505                 510

Leu Pro Ala Ser Thr Thr Ile Glu Tyr Lys Tyr Ile Arg Lys Phe Asn
                515                 520                 525

Gly Ala Val Thr Trp Glu Ser Asp Pro Asn Asn Ser Ile Thr Thr Pro
530                 535                 540

Ala Ser Gly Thr Phe Thr Gln Asn Asp Thr Trp Arg
545                 550                 555
```

US 9,963,690 B2

GLUCOAMYLASE VARIANTS AND POLYNUCLEOTIDES ENCODING SAME

CROSS-REFERENCE TO RELATED APPLICATIONS

This application is a 35 U.S.C. 371 national application of PCT/EP2014/058686 filed Apr. 29, 2014, which claims priority or the benefit under 35 U.S.C. 119 of Indian application no. 1933/CHE/2013 filed Apr. 30, 2013, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to glucoamylase variants, polynucleotides encoding the variants, methods of producing the variants, and methods of using the variants. Also described are the use of glucoamylases of the invention for starch conversion to produce fermentation products, such as ethanol, and syrups, such as glucose. The invention also relates to a composition comprising a glucoamylase of the invention.

Description of the Related Art

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus* being commercially most important.

Commercially, glucoamylases are used to convert starch containing material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese) industries.

The end product may also be a syrup. For instance, the end product may be glucose, but may also be converted, e.g., by a glucose isomerase to fructose or a mixture composed almost equally of glucose and fructose. This mixture, or a mixture further enriched with fructose, is the most commonly used high fructose corn syrup (HFCS) commercialized throughout the world.

It is an object of the present invention to provide polypeptides having glucoamylase activity and polynucleotides encoding the polypeptides and which provide a high yield in fermentation product production processes, such as ethanol production processes, including one-step ethanol fermentation processes from un-gelatinized raw (or uncooked) starch.

WO2006/069289 discloses glucoamylases derived from *Trametes cingulata, Pachykytospora papyracea* and *Leucopaxillus giganteus* and the use thereof in processes for manufacturing fermentation products.

The present invention provides glucoamylase variants with improved properties compared to its parent.

SUMMARY OF THE INVENTION

The present invention relates to glucoamylase variant comprising a substitution at one or more positions corresponding to positions 45, 46, 61, 86, 119, 120, 318 and 348 of the polypeptide of SEQ ID NO: 3, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3.

The present invention also relates to isolated polynucleotides encoding the variants; nucleic acid constructs, vectors, and host cells comprising the polynucleotides; and methods of producing the variants.

The present invention also relates to compositions comprising the glucoamylase variant of the invention.

The present invention further relates to a use of the glucoamylase variant of the invention for producing a syrup or a fermentation product.

The present invention further relates to a process of producing a fermentation product from starch-containing material comprising the steps of: (a) liquefying starch-containing material in the presence of an alpha amylase; (b) saccharifying the liquefied material; and (c) fermenting with a fermenting organism; wherein step (a) and/or step (b) is carried out using at least a glucoamylase variant.

The present invention still further relates to a process of producing a fermentation product from starch-containing material, comprising the steps of: (a) saccharifying starch-containing material at a temperature below the initial gelatinization temperature of said starch-containing material; and (b) fermenting with a fermenting organism, wherein step (a) is carried out using at least a glucoamylase variant.

DEFINITIONS

Glucoamylase: The term "glucoamylase" (1,4-alpha-D-glucan glucohydrolase, EC 3.2.1.3) is defined as an enzyme, which catalyzes the release of D-glucose from the non-reducing ends of starch or related oligo- and polysaccharide molecules. For purposes of the present invention, glucoamylase activity is determined according to the procedure described in the Examples herein. The Glucoamylase Unit (AGU) is defined as the amount of enzyme, which hydrolyses 1 micromole maltose per minute under the standard conditions 37° C., pH 4.3, substrate: maltose 23.2 mM, buffer: acetate 0.1 M, reaction time 5 minutes.

The polypeptides of the present invention have at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the mature polypeptide of SEQ ID NO: 2.

In another embodiment the polypeptides of the present invention have at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the polypeptide of SEQ ID NO: 3.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has glucoamylase activity. In one aspect, a fragment contains at least 450 amino acid residues (e.g., amino acids 23 to 472 of SEQ ID NO: 2) comprising the catalytic domain and having one or more of the substitutions according to the invention.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such an improved property is thermostability.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 19 to 574 of SEQ ID NO: 2 and amino acids 1 to 18 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide. The mature polypeptide is disclosed herein as SEQ ID NO: 3.

Mature polypeptide coding sequence: The term "mature polypeptide coding sequence" means a polynucleotide that encodes a mature polypeptide having glucoamylase activity. In one aspect, the mature polypeptide coding sequence is nucleotides 55 to 1722 of SEQ ID NO: 1 and nucleotides 1 to 54 of SEQ ID NO: 1 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single-or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent [enzyme]: The term "parent" or "parent [glucoamylase]" means a glucoamylase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having glucoamylase activity. In one aspect, a subsequence comprises the catalytic domain and contains at least 1350 nucleotides (e.g., nucleotides 67 to 1416 of SEQ ID NO: 1).

Variant: The term "variant" means a polypeptide having glucoamylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position The variants of the present invention have at least 20%, e.g., at least 40%, at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the mature polypeptide of SEQ ID NO: 2 disclosed as SEQ ID NO: 3.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type glucoamylase: The term "wild-type" glucoamylase means a glucoamylase expressed by a naturally occurring microorganism, such as a bacterium, yeast, or filamentous fungus found in nature.

Conventions for Designation of Variants

For purposes of the present invention, the mature polypeptide disclosed in SEQ ID NO: 3 is used to determine the corresponding amino acid residue in another glucoamylase. The amino acid sequence of another glucoamylase is aligned with the mature polypeptide disclosed in SEQ ID NO: 3, and based on the alignment, the amino acid position number corresponding to any amino acid residue in the mature polypeptide disclosed in SEQ ID NO: 3 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another glucoamylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1194, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1197, *Nucleic Acids Res.* 25: 3389-3402). Even greater sensitivity can be achieved if the family or superfamily for the polypeptide has one or more representatives in the protein structure databases. Programs such as GenTHREADER (Jones, 1199, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1198, Proteins 33: 88-96) or combinatorial extension (Shindyalov and Bourne, 1198, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411 F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G-K-A |

Multiple Alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to glucoamylase variants, comprising an substitution at one or more positions corresponding to positions 45, 46, 61, 86, 119, 120, 318 and 348 of the polypeptide of SEQ ID NO: 3, wherein the variant has glucoamylase activity. In particular the variants have improved property compared to the glucoamylase disclosed as SEQ ID NO: 3. Particularly, the improved property is increased thermo-stability. The variants according to the invention have at least 75%, at least 80%, at least 85%, at least 90%, at least 95%, at least 96%, at least 97%, at least 98%, or at least 99%, but less than 100% sequence identity to the polypeptide of SEQ ID NO: 3.

The mature polypeptide of SEQ ID NO: 2 corresponds to SEQ ID NO: 3. Thus the position numbers referred to herein correspond to the position numbers of SEQ ID NO: 3.

Variants

The present invention provides glucoamylase variants, comprising an substitution at one or more (e.g., several) positions corresponding to positions 45, 46, 61, 86, 119, 120, 318 and 348 and the variant has glucoamylase activity.

In one embodiment, the variant is isolated.

In another embodiment, the variant has sequence identity of at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent glucoamylase.

In yet another embodiment, the variant has at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 2. The mature polypeptide of SEQ ID NO: 2 is in one embodiment of SEQ ID NO: 3.

In a further embodiment, the present invention relates to a glucoamylase variant comprising a substitution at one or more positions corresponding to positions 45, 46, 61, 86, 119, 120, 318 and 348 of the polypeptide of SEQ ID NO: 3, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3. In one aspect, the number of susbtitutions in the variants of the present invention is 1-20, e.g., 1-10 and 1-5, such as 1, 2, 3, 4, 5, 6, 7, 8, 9 or 10 alterations.

In another aspect, a variant comprises an susbtitution at one or more positions corresponding to positions 45, 46, 61, 86, 119, 120, 318 and 348. In another aspect, a variant comprises an substitution at two positions corresponding to any of positions 45, 46, 61, 86, 119, 120, 318 and 348. In another aspect, a variant comprises an substitution at three positions corresponding to any of positions 45, 46, 61, 86, 119, 120, 318 and 348. In another aspect, a variant comprises an substitution at four positions corresponding to any of positions 45, 46, 61, 86, 119, 120, 318 and 348. In another aspect, a variant comprises an substitution at five positions corresponding to any of positions 45, 46, 61, 86, 119, 120, 318 and 348. In another aspect, a variant comprises an substitution at six positions corresponding to any of positions 45, 46, 61, 86, 119, 120, 318 and 348. In another aspect, a variant comprises an susbtitution at each position corresponding to positions 45, 46, 61, 86, 119, 120, 318 and 348.

In another aspect, the variant comprises or consists of a substitution at a position corresponding to position 45. In another aspect, the amino acid at a position corresponding to position 45 is substituted with Ala, Arg, Asn, Asp, Cys, Gln, Glu, Gly, His, Ile, Leu, Lys, Met, Phe, Pro, Ser, Trp, Tyr, or Val, preferably with Lys. In another aspect, the variant comprise or consist of the substitution T45K of the mature polypeptide of SEQ ID NO: 3.

In another aspect, the variant comprises or consists of a substitution at a position corresponding to position 46. In another aspect, the amino acid at a position corresponding to position 46 is substituted with Ala, Arg, Asn, Asp, Cys, Gln, Glu, Gly, His, Ile, Leu, Lys, Met, Phe, Pro, Thr, Trp, Tyr, or Val, preferably with His. In another aspect, the variant comprise or consist of the substitution S46H of the mature polypeptide of SEQ ID NO: 3.

In another aspect, the variant comprises or consists of a substitution at a position corresponding to position 61. In another aspect, the amino acid at a position corresponding to position 61 is substituted with Ala, Arg, Asn, Asp, Cys, Gln, Glu, Gly, His, Ile, Leu, Lys, Met, Phe, Pro, Ser, Thr, Trp or Tyr, preferably with Thr or Ala. In another aspect, the variant comprise or consist of the substitution V61T or V61A of the mature polypeptide of SEQ ID NO: 3.

In another aspect, the variant comprises or consists of a substitution at a position corresponding to position 86. In another aspect, the amino acid at a position corresponding to position 86 is substituted with Ala, Arg, Asn, Asp, Cys, Gln, Glu, Gly, His, Ile, Leu, Lys, Met, Phe, Pro, Thr, Trp, Tyr, or Val, preferably with Cys. In another aspect, the variant comprise or consist of the substitution S86C of the mature polypeptide of SEQ ID NO: 3.

In another aspect, the variant comprises or consists of a substitution at a position corresponding to position 119. In another aspect, the amino acid at a position corresponding to position 119 is substituted with Ala, Arg, Asn, Asp, Cys, Gln, Glu, Gly, His, Ile, Leu, Lys, Met, Phe, Pro, Ser, Trp, Tyr, or Val, preferably with Trp. In another aspect, the variant comprise or consist of the substitution T119W of the mature polypeptide of SEQ ID NO: 3.

In another aspect, the variant comprises or consists of a substitution at a position corresponding to position 120. In another aspect, the amino acid at a position corresponding to position 120 is substituted with Ala, Arg, Asn, Cys, Gln, Glu, Gly, His, Ile, Leu, Lys, Met, Phe, Pro, Ser, Thr, Trp, Tyr, or Val, preferably with Gly. In another aspect, the variant comprise or consist of the substitution D120G of the mature polypeptide of SEQ ID NO: 3.

In another aspect, the variant comprises or consists of a substitution at a position corresponding to position 318. In another aspect, the amino acid at a position corresponding to position 318 is substituted with Ala, Arg, Asn, Asp, Cys, Gln, Glu, Gly, His, Ile, Leu, Lys, Phe, Pro, Ser, Thr, Trp, Tyr, or Val, preferably with Trp. In another aspect, the variant comprise or consist of the substitution M318W of the mature polypeptide of SEQ ID NO: 3.

In another aspect, the variant comprises or consists of a substitution at a position corresponding to position 348. In another aspect, the amino acid at a position corresponding to position 348 is substituted with Ala, Arg, Asp, Cys, Gln, Glu, Gly, His, Ile, Leu, Lys, Met, Phe, Pro, Ser, Thr, Trp, Tyr, or Val, preferably with Thr. In another aspect, the variant comprise or consist of the substitution N348T of the mature polypeptide of SEQ ID NO: 3.

In another aspect, the variant comprises or consists of substitutions at positions corresponding to positions 45 and 46, such as those described above.

In another aspect, the variant comprises or consists of substitutions at positions corresponding to positions 45 and 61, such as those described above.

In another aspect, the variant comprises or consists of substitutions at positions corresponding to positions 45 and 86, such as those described above.

In another aspect, the variant comprises or consists of substitutions at positions corresponding to positions 45 and 119, such as those described above.

In another aspect, the variant comprises or consists of substitutions at positions corresponding to positions 45 and 120, such as those described above.

In another aspect, the variant comprises or consists of substitutions at positions corresponding to positions 45 and 318, such as those described above.

In another aspect, the variant comprises or consists of substitutions at positions corresponding to positions 45 and 348, such as those described above.

In another aspect, the variant comprises or consists of substitutions at positions corresponding to positions 46 and 61, such as those described above.

In another aspect, the variant comprises or consists of substitutions at positions corresponding to positions 46 and 86, such as those described above.

In another aspect, the variant comprises or consists of substitutions at positions corresponding to positions 46 and 119, such as those described above.

In another aspect, the variant comprises or consists of substitutions at positions corresponding to positions 46 and 120, such as those described above.

In another aspect, the variant comprises or consists of substitutions at positions corresponding to positions 46 and 318, such as those described above.

In another aspect, the variant comprises or consists of substitutions at positions corresponding to positions 46 and 348, such as those described above.

In another aspect, the variant comprises or consists of substitutions at positions corresponding to positions 61 and 86, such as those described above.

In another aspect, the variant comprises or consists of substitutions at positions corresponding to positions 61 and 119, such as those described above.

In another aspect, the variant comprises or consists of substitutions at positions corresponding to positions 61 and 120, such as those described above.

In another aspect, the variant comprises or consists of substitutions at positions corresponding to positions 61 and 318, such as those described above.

In another aspect, the variant comprises or consists of substitutions at positions corresponding to positions 61 and 348, such as those described above.

In another aspect, the variant comprises or consists of substitutions at positions corresponding to positions 86 and 119, such as those described above.

In another aspect, the variant comprises or consists of substitutions at positions corresponding to positions 86 and 120, such as those described above.

In another aspect, the variant comprises or consists of substitutions at positions corresponding to positions 86 and 318, such as those described above.

In another aspect, the variant comprises or consists of substitutions at positions corresponding to positions 86 and 348, such as those described above.

In another aspect, the variant comprises or consists of substitutions at positions corresponding to positions 119 and 120, such as those described above.

In another aspect, the variant comprises or consists of substitutions at positions corresponding to positions 119 and 318, such as those described above.

In another aspect, the variant comprises or consists of substitutions at positions corresponding to positions 119 and 348, such as those described above.

In another aspect, the variant comprises or consists of substitutions at positions corresponding to positions 120 and 318, such as those described above.

In another aspect, the variant comprises or consists of substitutions at positions corresponding to positions 120 and 348, such as those described above.

In another aspect, the variant comprises or consists of substitutions at positions corresponding to positions 318 and 348, such as those described above.

In another aspect, the variant comprises or consists of substitutions at positions corresponding to positions 45 and 46 and 61, such as those described above.

In another aspect, the variant comprises or consists of substitutions at positions corresponding to positions 45 and 46 and 86, such as those described above.

In another aspect, the variant comprises or consists of substitutions at positions corresponding to positions 45 and 46 and 119, such as those described above.

In another aspect, the variant comprises or consists of substitutions at positions corresponding to positions 45 and 46 and 120, such as those described above.

In another aspect, the variant comprises or consists of substitutions at positions corresponding to positions 45 and 46 and 318, such as those described above.

In another aspect, the variant comprises or consists of substitutions at positions corresponding to positions 45 and 46 and 348, such as those described above.

In another aspect, the variant comprises or consists of substitutions at positions corresponding to positions 45 and 61 and 86, such as those described above.

In another aspect, the variant comprises or consists of substitutions at positions corresponding to positions 45 and 61 and 119, such as those described above.

In another aspect, the variant comprises or consists of substitutions at positions corresponding to positions 45 and 61 and 120, such as those described above.

In another aspect, the variant comprises or consists of substitutions at positions corresponding to positions 45 and 61 and 318, such as those described above.

In another aspect, the variant comprises or consists of substitutions at positions corresponding to positions 45 and 61 and 348, such as those described above.

In another aspect, the variant comprises or consists of substitutions at positions corresponding to positions 45 and 86 and 119, such as those described above.

In another aspect, the variant comprises or consists of substitutions at positions corresponding to positions 45 and 86 and 120, such as those described above.

In another aspect, the variant comprises or consists of substitutions at positions corresponding to positions 45 and 86 and 318, such as those described above.

In another aspect, the variant comprises or consists of substitutions at positions corresponding to positions 45 and 86 and 348, such as those described above.

In another aspect, the variant comprises or consists of substitutions at positions corresponding to positions 45 and 119 and 120, such as those described above.

In another aspect, the variant comprises or consists of substitutions at positions corresponding to positions 45 and 119 and 318, such as those described above.

In another aspect, the variant comprises or consists of substitutions at positions corresponding to positions 45 and 119 and 348, such as those described above.

In another aspect, the variant comprises or consists of substitutions at positions corresponding to positions 45 and 120 and 318, such as those described above.

In another aspect, the variant comprises or consists of substitutions at positions corresponding to positions 45 and 120 and 348, such as those described above.

In another aspect, the variant comprises or consists of substitutions at positions corresponding to positions 45 and 318 and 348, such as those described above.

In another aspect, the variant comprises or consists of substitutions at positions corresponding to positions 46 and 61 and 86, such as those described above.

In another aspect, the variant comprises or consists of substitutions at positions corresponding to positions 46 and 61 and 119, such as those described above.

In another aspect, the variant comprises or consists of substitutions at positions corresponding to positions 46 and 61 and 120, such as those described above.

In another aspect, the variant comprises or consists of substitutions at positions corresponding to positions 46 and 61 and 318, such as those described above.

In another aspect, the variant comprises or consists of substitutions at positions corresponding to positions 46 and 61 and 348, such as those described above.

In another aspect, the variant comprises or consists of substitutions at positions corresponding to positions 46 and 61 and 119, such as those described above.

In another aspect, the variant comprises or consists of substitutions at positions corresponding to positions 46 and 61 and 120, such as those described above.

In another aspect, the variant comprises or consists of substitutions at positions corresponding to positions 46 and 86 and 318, such as those described above.

In another aspect, the variant comprises or consists of substitutions at positions corresponding to positions 46 and 86 and 348, such as those described above.

In another aspect, the variant comprises or consists of substitutions at positions corresponding to positions 46 and 119 and 120, such as those described above.

In another aspect, the variant comprises or consists of substitutions at positions corresponding to positions 46 and 119 and 318, such as those described above.

In another aspect, the variant comprises or consists of substitutions at positions corresponding to positions 46 and 119 and 348, such as those described above.

In another aspect, the variant comprises or consists of substitutions at positions corresponding to positions 46 and 120 and 318, such as those described above.

In another aspect, the variant comprises or consists of substitutions at positions corresponding to positions 46 and 120 and 348, such as those described above.

In another aspect, the variant comprises or consists of substitutions at positions corresponding to positions 46 and 318 and 348, such as those described above.

In another aspect, the variant comprises or consists of substitutions at positions corresponding to positions 61 and 86 and 119, such as those described above.

In another aspect, the variant comprises or consists of substitutions at positions corresponding to positions 61 and 86 and 120, such as those described above.

In another aspect, the variant comprises or consists of substitutions at positions corresponding to positions 61 and 86 and 318, such as those described above.

In another aspect, the variant comprises or consists of substitutions at positions corresponding to positions 61 and 86 and 348, such as those described above.

In another aspect, the variant comprises or consists of substitutions at positions corresponding to positions 61 and 119 and 120, such as those described above.

In another aspect, the variant comprises or consists of substitutions at positions corresponding to positions 61 and 119 and 318, such as those described above.

In another aspect, the variant comprises or consists of substitutions at positions corresponding to positions 61 and 119 and 348, such as those described above.

In another aspect, the variant comprises or consists of substitutions at positions corresponding to positions 61 and 120 and 318, such as those described above.

In another aspect, the variant comprises or consists of substitutions at positions corresponding to positions 61 and 120 and 348, such as those described above.

In another aspect, the variant comprises or consists of substitutions at positions corresponding to positions 61 and 318 and 348, such as those described above.

In another aspect, the variant comprises or consists of substitutions at positions corresponding to positions 86 and 119 and 120, such as those described above.

In another aspect, the variant comprises or consists of substitutions at positions corresponding to positions 86 and 119 and 318, such as those described above.

In another aspect, the variant comprises or consists of substitutions at positions corresponding to positions 86 and 119 and 348, such as those described above.

In another aspect, the variant comprises or consists of substitutions at positions corresponding to positions 86 and 120 and 318, such as those described above.

In another aspect, the variant comprises or consists of substitutions at positions corresponding to positions 86 and 120 and 348, such as those described above.

In another aspect, the variant comprises or consists of substitutions at positions corresponding to positions 86 and 318 and 348, such as those described above.

In another aspect, the variant comprises or consists of substitutions at positions corresponding to positions 119 and 120 and 318, such as those described above.

In another aspect, the variant comprises or consists of substitutions at positions corresponding to positions 119 and 120 and 348, such as those described above.

In another aspect, the variant comprises or consists of substitutions at positions corresponding to positions 119 and 318 and 348, such as those described above.

In another aspect, the variant comprises or consists of substitutions at positions corresponding to positions 120 and 318 and 348, such as those described above.

In another aspect, the variant comprises or consists of one or more substitutions selected from the group consisting of T45K; S46H; V61T; S86C; T119W; D120G; M318W and N348T and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3.

In another aspect, the variant comprises or consists of the below listed specific substitutions or combinations of specific substutions of the mature polypeptide of SEQ ID NO: 3.

T119W;
D120G;
V61A;
S86C+T119W;
T45K+T119W;
T119W+D120G;
T45K+D120G;
V61T+T119W;
D120G+M318W;
T45K+S46H;
T119W+D120G+N348T;
T119W+D120G+M318W;
S86C+T119W+D120G;
S46H+T119W+D120G;
T45K+T119W+D120G and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution T119W of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution D120G of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution S86C+T119W of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution T45K+T119W of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution T119W+D120G of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution T45K+D120G of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution V61T+T119W of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution D120G+M318W of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution T45K+S46H of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution T119W+D120G+N348T of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution T119W+D120G+M318W of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution S86C+T119W+D120G of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution S46H+T119W+D120G of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

More specifically the invention relates in one embodiment to glucoamylase variants, comprising the substitution T45K+T119W+D120G of the polypeptide of SEQ ID NO: 3, wherein the variant has glucoamylase activity, and wherein the glucoamylase variants have at least 75%, at least 80%, at least 85%, at least 90%, at least 95%, at least 96%, at least 97%, at least 98%, or at least 99%, but less than 100% sequence identity to the polypeptide of SEQ ID NO: 3.

All of the above specific substitutions or combinations of substitutions have an effect of increasing the thermo-stability of the resulting variant when introduced in the parent disclosed as SEQ ID NO: 3.

The variants may further comprise one or more additional substitutions at one or more (e.g., several) other positions. Such further variation could be introduced without affecting significantly the properties of the glucoamylase variants.

Therefore the % identity of the variant polypeptide compared to the parent polypeptide of SEQ ID NO: 3 may be at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3.

In one particular embodiment the above variants have glucoamylase activity, and the variant has at least 75%, but less than 100%, sequence identity to the polypeptide of SEQ ID NO: 3.

In one particular embodiment the above variants have glucoamylase activity, and the variant has at least 80%, but less than 100%, sequence identity to the polypeptide of SEQ ID NO: 3.

In one particular embodiment the above variants have glucoamylase activity, and the variant has at least 85%, but less than 100%, sequence identity to the polypeptide of SEQ ID NO: 3.

In one particular embodiment the above variants have glucoamylase activity, and the variant has at least 90%, but less than 100%, sequence identity to the polypeptide of SEQ ID NO: 3.

In one particular embodiment the above variants have glucoamylase activity, and the variant has at least 91%, but less than 100%, sequence identity to the polypeptide of SEQ ID NO: 3.

In one particular embodiment the above variants have glucoamylase activity, and the variant has at least 92%, but less than 100%, sequence identity to the polypeptide of SEQ ID NO: 3.

In one particular embodiment the above variants have glucoamylase activity, and the variant has at least 93%, but less than 100%, sequence identity to the polypeptide of SEQ ID NO: 3.

In one particular embodiment the above variants have glucoamylase activity, and the variant has at least 94%, but less than 100%, sequence identity to the polypeptide of SEQ ID NO: 3.

In one particular embodiment the above variants have glucoamylase activity, and the variant has at least 95%, but less than 100%, sequence identity to the polypeptide of SEQ ID NO: 3.

In one particular embodiment the above variants have glucoamylase activity, and the variant has at least 96%, but less than 100%, sequence identity to the polypeptide of SEQ ID NO: 3.

In one particular embodiment the above variants have glucoamylase activity, and the variant has at least 97%, but less than 100%, sequence identity to the polypeptide of SEQ ID NO: 3.

In one particular embodiment the above variants have glucoamylase activity, and the variant has at least 98%, but less than 100%, sequence identity to the polypeptide of SEQ ID NO: 3.

In one particular embodiment the above variants have glucoamylase activity, and the variant has at least 99%, but less than 100%, sequence identity to the polypeptide of SEQ ID NO: 3.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for glucoamylase activity to identify amino acid residues that are critical to the activity of the molecule. See also, Hilton et al., 1196, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1192, Science 255: 306-312; Smith et al., 1192, J. Mol. Biol. 224: 899-904; Wlodaver et al., 1192, FEBS Lett. 309: 59-64. The identity of essential amino acids can also be inferred from an alignment with a related polypeptide.

In an embodiment, the variant has improved thermostability compared to the parent enzyme. The improved thermostability may be determined by measuring the residual glucoamylase activity as disclosed in the examples.

Parent Glucoamylase

The parent glucoamylase may be (a) a polypeptide having at least 70% sequence identity to the mature polypeptide of SEQ ID NO: 2; (b) a polypeptide encoded by a polynucleotide that hybridizes under low stringency conditions with (i) the mature polypeptide coding sequence of SEQ ID NO: 1, or (ii) the full-length complement of (i) or (c) a polypeptide encoded by a polynucleotide having at least 70% sequence identity to the mature polypeptide coding sequence of SEQ ID NO: 1.

In an aspect, the parent has a sequence identity to the mature polypeptide of SEQ ID NO: 2 of at least 75%, at least 80%, at least 85%, at least 90%, at least 91%, at least 92%, at least 93%, at least 94%, at least 95%, at least 96%, at least 97%, at least 98%, at least 99%, or 100%, which have glucoamylase activity. In one aspect, the amino acid sequence of the parent differs by up to 10 amino acids, e.g., 1, 2, 3, 4, 5, 6, 7, 8, 9, or 10, from the mature polypeptide of SEQ ID NO: 2.

In another aspect, the parent comprises or consists of the amino acid sequence of SEQ ID NO: 2. In another aspect, the parent comprises or consists of the mature polypeptide of SEQ ID NO: 2. In another aspect, the parent comprises or consists of amino acids 18 to 574 of SEQ ID NO: 2.

In another aspect, the parent is a fragment of the mature polypeptide of SEQ ID NO: 2 containing at least 450 amino acid residues, e.g., at least 23 and at least 472 amino acid residues.

In another embodiment, the parent is an allelic variant of the mature polypeptide of SEQ ID NO: 2.

In another aspect, the parent is encoded by a polynucleotide that hybridizes under high stringency conditions, or very high stringency conditions with (i) the mature polypeptide coding sequence of SEQ ID NO: 1, or (ii) the full-length complement of (i) (Sambrook et al., 1989, Molecular Cloning, A Laboratory Manual, 2d edition, Cold Spring Harbor, N.Y.).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$. biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iiii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 55 to 1722 of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In another embodiment, the parent is encoded by a polynucleotide having a sequence identity to the mature polypeptide coding sequence of SEQ ID NO: 1 at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1193, *EMBO J.* 12: 2575-2583; Dawson et al., 1194, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1197, *Appl. Environ. Microbiol.* 63: 3488-3493; Ward et al., 1195, *Biotechnology* 13: 498-503; and Contreras et al., 1191, *Biotechnology* 9: 378-381; Eaton et al., 1986, *Biochemistry* 25: 505-512; Collins-Racie et al., 1195, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a fungal glucoamylase. For example, the parent may be a *Trametes* glucoamylase.

In another aspect, the parent is a *Trametes cingulate* glucoamylase.

In another aspect, the parent is a *Trametes cingulata* glucoamylase e.g., the glucoamylase of SEQ ID NO: 2 or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1190, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1198, *Nat. Med.* 4: 285-290; and Calissano and Macino, 1196, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1191, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1199, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant.

The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1194, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1192, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1192, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1195, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1195, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1193, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1192, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1191, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1191, *Microbios* 68: 189-207), electroporation (see, e.g., Buckley et al., 1199, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1195, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1195, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The present invention also relates to compositions comprising a polypeptide of the present invention. Preferably the composition also comprises a carrier and/or an excipient. More preferably, the compositions are enriched in such a polypeptide. The term "enriched" indicates that the glucoamylase activity of the composition has been increased, e.g., with an enrichment factor of at least 1.1. Preferably, the compositions are formulated to provide desirable characteristics such as low color, low odor and acceptable storage stability.

The composition may comprise a polypeptide of the present invention as the major enzymatic component, e.g., a mono-component composition. Alternatively, the composition may comprise multiple enzymatic activities, such as an aminopeptidase, alpha-amylase, isoamylase carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, pullulanase, proteolytic enzyme, ribonuclease, transglutaminase, or xylanase.

In a particular embodiment the composition comprises an alpha-amylase and glucoamylase variant according to the invention. In another embodiment the composition comprises an isoamylase and glucoamylase variant according to the invention. In another embodiment the composition comprises an alpha-amylase, an isoamylase and the glucoamylase variant according to the invention.

In another aspect the composition comprises the glucoamylase variant of the invention combined with a pullulanase. In another aspect the composition comprises the glucoamylase variant of the invention combined with a pullulanase, and an isoamylase. In another aspect the composition comprises the glucoamylase variant of the invention combined with a pullulanase, and an alpha-amylase.

In a particular embodiment the composition further comprises a protease.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art. Examples are given below of preferred uses of the polypeptide or polypeptide compositions of the invention. The dosage of the polypeptide composition of the invention and other conditions under which the composition is used may be determined on the basis of methods known in the art.

The above compositions are suitable for use in liquefaction, saccharification, and/or fermentation processes, preferably in starch conversion, especially for producing syrup and fermentation products, such as ethanol.

Examples are given below of preferred uses of the polypeptide compositions of the present invention. The dosage of the polypeptide composition of the invention and other conditions under which the composition is used may be determined on the basis of methods known in the art.

Uses

The present invention is also directed to use of a polypeptide of the present invention in a liquefaction, a saccharification and/or a fermentation process. The polypeptide may be used in a single process, for example, in a liquefaction process, a saccharification process, or a fermentation process. The polypeptide may also be used in a combination of processes for example in a liquefaction and saccharification process, in a liquefaction and fermentation process, or in a saccharification and fermentation process, preferably in relation to starch conversion.

In a preferred aspect of the present invention, the liquefaction, saccharification and/or fermentation process includes sequentially or simultaneously performed liquefaction and saccharification processes.

In conventional enzymatic liquefaction process, thermostable alpha-amylase is added and the long chained starch is degraded into branched and linear shorter units (maltodextrins), but glucoamylase is not added. The glucoamylase of the present invention is highly thermostable, so it is advantageous to add the glucoamylase in the liquefaction process.

The glucoamylase of the present invention has a synergistic effect when combined with an alpha-amylase in the liquefaction process. During conventional saccharification, the dextrins generated during the liquefaction process are further hydrolyzed to produce low molecular sugars DP1-3 that can be metabolized by fermenting organism. The hydrolysis is typically accomplished using glucoamylases; alternatively in addition to glucoamylases, alpha-glucosidases and/or acid alpha-amylases can be used.

When applying the glucoamylase of the present invention, potentially in combination with an alpha-amylase in a liquefaction and/or saccharification process, especially in a simultaneous liquefaction and saccharification process, the process can be conducted at a higher temperature. In another aspect the composition comprises the glucoamylase variant of the invention combined with a pullulanase. In another aspect the composition comprises the glucoamylase variant of the invention combined with a pullulanase, and an isoamylase. In another aspect the composition comprises the glucoamylase variant of the invention combined with a pullulanase, and an alpha-amylase.

By conducting the liquefaction and/or saccharification process at higher temperatures the process can be carried out in a shorter period of time or alternatively the process can be carried out using lower enzyme dosage. Furthermore, the risk of microbial contamination is reduced when carrying the liquefaction and/or saccharification process at higher temperature.

Conversion of Starch-Containing Material

The present invention provides a use of the glucoamylase of the invention for producing glucoses and the like from starch. Generally, the method includes the steps of partially hydrolyzing precursor starch using glucoamylase variant of the present invention either alone or in the presence of an alpha-amylase.

The glucoamylase variant of the invention may also be used in combination with an enzyme that hydrolyzes only alpha-(1,6)-glucosidic bonds in molecules comprising at least four glucosyl residues.

In a further aspect the invention relates to the use of a glucoamylase of the invention in starch conversion. Furthermore, the glucoamylase of the invention may be used in a continuous starch conversion process including a continuous saccharification process.

Production of Syrup, Beverage and/or Fermentation Product

Uses of the glucoamylase of the invention include conversion of starch to e.g., syrup beverage, and/or a fermentation product, including ethanol.

The present invention also provides a process of using a glucoamylase of the invention for producing syrup, such as glucose and the like, from starch-containing material. Suitable starting materials are exemplified in the "Starch-containing materials"-section. Generally, the process comprises the steps of partially or totally hydrolyzing starch-containing material (liquefaction and/or saccharification) in the presence of the glucoamylase of the present invention alone or in combination with alpha-amylase to release glucose from the non-reducing ends of the starch or related oligo- and poly-saccharide molecules.

The glucoamylase variant of the invention may also be used in immobilized form. This is suitable and often used for producing speciality syrups, such as maltose syrups as well as in the raffinate stream of oligosaccharides in connection with the production of fructose syrups, e.g., high fructose syrup (HFS).

Fermentation Products

The term "fermentation product" means a product produced by a process including a fermentation process using a fermenting organism. Fermentation products contemplated according to the invention include alcohols (e.g., arabinitol, butanol, ethanol, glycerol, methanol, ethylene glycol, 1,3-propanediol [propylene glycol], butanediol, glycerin, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); ketones (e.g., acetone); amino acids (e.g., aspartic acid, glutamic acid, glycine, lysine, serine, and threonine); an alkane (e.g., pentane, hexane, heptane, octane, nonane, decane, undecane, and dodecane); a cycloalkane (e.g., cyclopentane, cyclohexane, cycloheptane, and cyclooctane); an alkene (e.g. pentene, hexene, heptene, and octene); gases (e.g., methane, hydrogen ($H_2$), carbon dioxide ($CO_2$), and carbon monoxide (CO)); antibiotics (e.g., penicillin and tetracycline); enzymes; vitamins (e.g., riboflavin, $B_{12}$, beta-carotene); and hormones. In a preferred aspect the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes, which are well known in the art. Preferred fermentation processes are anaerobic fermentation processes, which are well known in the art.

Brewing

The glucoamylases of the present invention are highly thermostable and therefore they can be used in an industry which needs starch hydrolysis at high temperature. For example, glucoamylases of the invention can be used in a brewing industry. The glucoamylases of the invention is added in effective amounts which can be easily determined by the skilled person in the art.

Production of a Liquefaction, Saccharification and/or Fermentation Product

In this aspect the present invention relates to a process for producing a liquefaction, saccharification and/or fermentation product from starch-containing material, comprising the step of: treating starch-containing material with a polypeptide of the present invention.

Suitable starch-containing starting materials are listed in the "Starch-containing materials"-section below. Contemplated enzymes are listed in the "Enzymes"—section below. Preferably the process of present invention comprises treating starch-containing material with a polypeptide of the present invention alone or together with an alpha-amylase. The liquefaction and/or saccharification product of the present invention are dextrin, or low molecular sugars, for example DP1-3. In the liquefaction process the conversion of starch into glucose, dextrin and/or low molecular weight sugars is enhanced by the addition of a glucoamylase of the present invention. The fermentation product, such as ethanol, may optionally be recovered after fermentation, e.g., by distillation. The fermentation is preferably carried out in the presence of yeast, preferably a strain of *Saccharomyces*. Suitable fermenting organisms are listed in the "Fermenting Organisms"-section below.

Process for Producing Fermentation Products from Gelatinized Starch Containing Material In this aspect the present invention relates to a process for producing a fermentation product, especially ethanol, from starch-containing material, which process includes a liquefaction step and sequentially or simultaneously performed saccharification and fermentation steps.

The invention relates to a process for producing a fermentation product from starch-containing material comprising the steps of:
(a) liquefying starch-containing material; using an alpha amylase;
(b) saccharifying the liquefied material obtained in step (a) using a glucoamylase; and
(c) fermenting the saccharified material using a fermenting organism.

Preferably step (a) includes also using the glucoamylase of the invention. In one embodiment the glucoamylase of the invention is also present/added in step (b).

The fermentation product, such as especially ethanol, may optionally be recovered after fermentation, e.g., by distillation. Suitable starch-containing starting materials are listed in the section "Starch-containing materials"-section below. Contemplated enzymes are listed in the "Enzymes"-section below. The liquefaction is preferably carried out in the presence of an alpha-amylase. The fermentation is preferably carried out in the presence of yeast, preferably a strain of *Saccharomyces*. Suitable fermenting organisms are listed in the "Fermenting Organisms"-section below. In preferred embodiments step (b) and (c) are carried out sequentially or simultaneously (i.e., as SSF process).

In a particular embodiment, the process of the invention further comprises, prior to the step (a), the steps of:
x) reducing the particle size of the starch-containing material, preferably by milling; and
y) forming a slurry comprising the starch-containing material and water.

The aqueous slurry may contain from 10-40 wt. %, preferably 25-35 wt. % starch-containing material. The slurry is heated to above the gelatinization temperature and alpha-amylase, preferably bacterial and/or acid fungal alpha-amylase, may be added to initiate liquefaction (thinning). The slurry may in an embodiment be jet-cooked to further gelatinize the slurry before being subjected to an alpha-amylase in step (a) of the invention.

More specifically liquefaction may be carried out as a three-step hot slurry process. The slurry is heated to between 60-95° C., preferably 80-85° C., and alpha-amylase is added to initiate liquefaction (thinning). Then the slurry may be jet-cooked at a temperature between 95-140° C., preferably 105-125° C., for 1-15 minutes, preferably for 3-10 minute, especially around 5 minutes. The slurry is cooled to 60-95° C. and more alpha-amylase is added to finalize hydrolysis (secondary liquefaction). The liquefaction process is usually carried out at pH 4.5-6.5, in particular at a pH between 5 and 6. Milled and liquefied whole grains are known as mash.

The saccharification in step (b) may be carried out using conditions well know in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 30-65° C., typically around 60° C., and at a pH between 4 and 5, normally at about pH 4.5.

The most widely used process in fermentation product, especially ethanol, production is the simultaneous saccharification and fermentation (SSF) process, in which there is no holding stage for the saccharification, meaning that fermenting organism, such as yeast, and enzyme(s) may be added together. SSF may typically be carried out at a temperature between 25° C. and 40° C., such as between 29° C. and 35° C., such as between 30° C. and 34° C., such as around 32° C. According to the invention the temperature may be adjusted up or down during fermentation.

In accordance with the present invention the fermentation step (c) includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. Preferred fermentation processes include alcohol fermentation processes, as are well known in the art. Preferred fermentation processes are anaerobic fermentation processes, as are well known in the art.

Processes for Producing Fermentation Products from Un-gelatinized Starch-containinq In this aspect the invention relates to processes for producing a fermentation product from starch-containing material without gelatinization of the starch-containing material (i.e., uncooked starch-containing material). According to the invention the desired fermentation product, such as ethanol, can be produced without liquefying the aqueous slurry containing the starch-containing material. In one embodiment a process of the invention includes saccharifying (milled) starch-containing material, e.g., granular starch, below the gelatinization temperature in the presence of an alpha amylase to produce sugars that can be fermented into the desired fermentation product by a suitable fermenting organism. In another embodiment a glucoamylase of the invention and an alpha amylase are used during saccharification and fermentation. In one aspect the invention relates to a process for producing a fermentation product from starch-containing material comprising:
(a) saccharifying starch-containing material with a mature glucoamylase according to the invention, preferably having the sequence shown as amino acids 22 to 616 in SEQ ID NO: 2, at a temperature below the initial gelatinization temperature of said starch-containing material,
(b) fermenting using a fermenting organism.

Steps (a) and (b) of the process of the invention may be carried out sequentially or simultaneously. In an embodiment, a slurry comprising water and starch-containing material, is prepared before step (a).

In a preferred embodiment step (a) includes addition of an alpha amylase.

The fermentation process may be carried out for a period of 1 to 250 hours, preferably is from 25 to 190 hours, more preferably from 30 to 180 hours, more preferably from 40 to 170 hours, even more preferably from 50 to 160 hours, yet more preferably from 60 to 150 hours, even yet more preferably from 70 to 140 hours, and most preferably from 80 to 130 hours.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein and Lii, 1192, *Starch/Stärke* 44(12): 461-466.

Before step (a) a slurry of starch-containing material, such as granular starch, having 10-55 wt. % dry solids, preferably 25-40 wt. % dry solids, more preferably 30-35 wt. % dry solids of starch-containing material may be prepared. The slurry may include water and/or process waters, such as stillage (backset), scrubber water, evaporator condensate or distillate, side stripper water from distillation, or other fermentation product plant process water. Because the process of the invention is carried out below the gelatinization temperature and thus no significant viscosity increase takes place, high levels of stillage may be used if desired. In an embodiment the aqueous slurry contains from about 1 to about 70 vol. % stillage, preferably 15-60% vol. % stillage, especially from about 30 to 50 vol. % stillage.

The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the starch-containing material is converted into a soluble starch hydrolysate.

The process of the invention is conducted at a temperature below the initial gelatinization temperature. Preferably the temperature at which step (a) is carried out is between 30-75° C., preferably between 45-60° C.

In a preferred embodiment step (a) and step (b) are carried out as a sequential or simultaneous saccharification and fermentation process. In such preferred embodiment the process is typically carried at a temperature between 25° C. and 40° C., such as between 29° C. and 35° C., such as between 30° C. and 34° C., such as around 32° C. According to the invention the temperature may be adjusted up or down during fermentation.

In an embodiment simultaneous saccharification and fermentation is carried out so that the sugar level, such as glucose level, is kept at a low level such as below 6 wt. %, preferably below about 3 wt. %, preferably below about 2 wt. %, more preferred below about 1 wt. %., even more preferred below about 0.5 wt. %, or even more preferred 0.25 wt. %, such as below about 0.1 wt. %. Such low levels of sugar can be accomplished by simply employing adjusted quantities of enzyme and fermenting organism. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt. % or below about 0.2 wt. %.

The process may be carried out at a pH in the range between 3 and 7, preferably from pH 3.5 to 6, or more preferably from pH 4 to 5.

The glucoamylase of the present invention is highly thermostable, so the pre-saccharification and/or saccharification of the present invention can be carried at a higher temperature than the conventional pre-saccharification and/or saccharification. In one embodiment a process of the invention includes pre-saccharifying starch-containing material before simultaneous saccharification and fermentation (SSF) process. The pre-saccharification can be carried out at a high temperature (for example, 50-85° C., preferably 60-75° C.) before moving into SSF.

Starch-containing Materials

Any suitable starch-containing starting material, including granular starch, may be used according to the present invention. The starting material is generally selected based on the desired fermentation product. Examples of starch-containing starting materials, suitable for use in a process of present invention, include tubers, roots, stems, whole grains, corns, cobs, wheat, barley, rye, milo, sago, cassava, tapioca, sorghum, rice peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof. Contemplated are both waxy and non-waxy types of corn and barley.

Fermenting Organisms

"Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include fungal organisms, such as yeast. Preferred yeast includes strains of *Saccharomyces* spp., in particular, *Saccharomyces cerevisiae*. Commercially available yeast include, e.g., Red Star™/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Enzymes

Glucoamylase

The glucoamylase is preferably a glucoamylase of the invention. However, as mentioned above a glucoamylase of the invention may also be combined with other glucoamylases.

The glucoamylase may added in an amount of 0.001 to 10 AGU/g DS, preferably from 0.01 to 5 AGU/g DS, such as around 0.05, 0.1, 0.3, 0.5, 1 or 2 AGU/g DS, especially 0.05 to 0.5 AGU/g DS; or 0.02-20 AGU/g DS, preferably 0.1-10 AGU/g DS.

Alpha-Amylase

The alpha-amylase may according to the invention be of any origin. Preferred are alpha-amylases of fungal or bacterial origin.

In a preferred aspect the alpha-amylase is an acid alpha-amylase, e.g., fungal acid alpha-amylase or bacterial acid alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylases

According to the invention a bacterial alpha-amylase may preferably be derived from the genus *Bacillus*.

In a preferred aspect the *Bacillus* alpha-amylase is derived from a strain of *B. licheniformis, B. amyloliquefaciens, B. subtilis* or *B. stearothermophilus*, but may also be derived from other *Bacillus* sp. Specific examples of contemplated alpha-amylases include the *Bacillus licheniformis* alpha-amylase (BLA) shown in SEQ ID NO: 4 in WO 99/19467, the *Bacillus amyloliquefaciens* alpha-amylase (BAN) shown in SEQ ID NO: 5 in WO 99/19467, and the *Bacillus stearothermophilus* alpha-amylase (BSG) shown in SEQ ID NO: 3 in WO 99/19467. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 98% or at least 99% identity to any of the sequences shown as SEQ ID NOS: 1, 2, 3, 4, or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or 6,187,576 (hereby incorporated by reference) and include *Bacillus stearothermophilus* alpha-amylase (BSG alpha-amylase) variants having a deletion of one or two amino acid in position 179 to 182, preferably a double deletion disclosed in WO 1196/023873—see e.g., page 20, lines 1-10 (hereby incorporated by reference), preferably corresponding to delta (181-182) compared to the wild-type BSG alpha-amylase amino acid sequence set forth in SEQ ID NO: 3 disclosed in WO 99/19467 or deletion of amino acids 179 and 180 using SEQ ID NO: 3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta (181-182) and further comprise a N193F substitution (also denoted 1181*+G182*+N193F) compared to the wild-type BSG alpha-amylase amino acid sequence set forth in SEQ ID NO: 3 disclosed in WO 99/19467.

The alpha-amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic alpha-amylase from *Bacillus stearothermophilus* strain NCIB 11837 is commercially available from Novozymes NS, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the *Bacillus licheniformis* alpha-amylase (shown as SEQ ID NO: 4 in WO 99/19467) and the 37 N-terminal amino acid residues of the alpha-amylase derived from *Bacillus amyloliquefaciens* (shown as SEQ ID NO: 3 in WO 99/194676), with one or more, especially all, of the following substitutions: G48A+T49I+G107A+H156Y+A181T+N190F+I201F+A209V+Q264S (using the *Bacillus licheniformis* numbering). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

Fungal Alpha-Amylases

Fungal acid alpha-amylases include acid alpha-amylases derived from a strain of the genus *Aspergillus*, such as *Aspergillus oryzae*, *Aspergillus niger*, or *Aspergillus kawachii* alpha-amylases.

A preferred acid fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred aspect the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated.

In a preferred aspect the alpha-amylase is derived from *Aspergillus kawachii* and disclosed by Kaneko et al. J. Ferment. Bioeng. 81:292-298(1196) "Molecular-cloning and determination of the nucleotide-sequence of a gene encoding an acid-stable alpha-amylase from *Aspergillus kawachii*"; and further as EMBL:#AB008370.

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid alpha-amylase is derived from a strain of *Aspergillus kawachii*.

Fungal Hybrid Alpha-Amylases

In a preferred aspect the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or US patent application No. 2006/0148054 (Novozymes) which is hereby incorporated by reference. A hybrid alpha-amylase may comprise an alpha-amylase catalytic domain (CD) and a carbohydrate-binding domain/module (CBM) and optional a linker.

Specific examples of contemplated hybrid alpha-amylases include, but not limited to those disclosed in U.S. patent application No. 2006/0148054 including Fungamyl variant with catalytic domain JA118 and *Athelia rolfsii* SBD (SEQ ID NO: 100 in U.S. application No. 2006/0148054), *Rhizomucor pusillus* alpha-amylase with *Athelia rolfsii* AMG linker and SBD (SEQ ID NO: 101 in U.S. application No. 2006/0148054) and *Meripilus giganteus* alpha-amylase with *Athelia rolfsii* glucoamylase linker and SBD (SEQ ID NO: 102 in U.S. application No. 2006/0148054); and *Rhizomucor pusillus* alpha-amylase with *Aspergillus niger* glucoamylase linker and CBM (SEQ ID NO 2 in international publication No. WO2007/144424).

Other specific examples of contemplated hybrid alpha-amylases include, but not limited to those disclosed in U.S. Patent Publication no. 2005/0054071, including those disclosed in Table 3 on page 15, such as *Aspergillus niger* alpha-amylase with *Aspergillus kawachii* linker and starch binding domain.

Commercial Alpha-Amylase Products

Preferred commercial compositions comprising alpha-amylase include MYCOLASE from DSM (Gist Brocades), BAN™, TERMAMYL™ SC, FUNGAMYL™, LIQUOZYME™ SC, LIQUOZYME™ SC DS, and SAN™ SUPER, SAN™ EXTRA L (Novozymes NS) and CLARASE™ L-40,000, DEX-LO™, SPEZYME™ FRED, SPEZYME™ AA, SPEZYME™ Ethyl, and SPEZYME™ DELTA AA (Genencor Int.)

The present invention is further described by the following numbered paragraphs:

Paragraph[1]. A glucoamylase variant comprising a substitution at one or more positions corresponding to positions 45, 46, 61, 86, 119, 120, 318, 348 of the polypeptide of SEQ ID NO: 3 wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3.

Paragraph[2]. The variant of paragraph 1, which is a variant of a parent glucoamylase selected from the group consisting of: a polypeptide having at least 75% sequence identity to the mature polypeptide of SEQ ID NO: 2; a polypeptide encoded by a polynucleotide having at least 75% identity to the mature polypeptide coding sequence of SEQ ID NO: 1; and a fragment of the polypeptide of SEQ ID NO: 3, which has glucoamylase activity.

Paragraph[3]. The variant of paragraph 2, wherein the parent glucoamylase has at least 75%, at least 80%, at least 85%, at least 90%, at least 95%, at least 96%, at least 97%, at least 98%, at least 99% or 100% sequence identity to the polypeptide of SEQ ID NO: 3.

Paragraph[4]. The variant of any of paragraphs 2-3, wherein the parent glucoamylase is encoded by a polynucleotide having at least 75%, at least 80%, at least 85%, at least 90%, at least 95%, at least 96%, at least 97%, at least 98%, at least 99%, or 100% sequence identity to the mature polypeptide coding sequence of SEQ ID NO: 1.

Paragraph[5]. The variant of any of paragraphs 2-4, wherein the parent glucoamylase comprises or consists of the polypeptide of SEQ ID NO: 3.

Paragraph[6]. The variant of any of paragraphs 2-5, wherein the parent glucoamylase is a fragment of the mature polypeptide of SEQ ID NO: 3, wherein the fragment has glucoamylase activity.

Paragraph[7]. The variant of any of paragraphs 1-6, wherein the mature polypeptide of SEQ ID NO: 2 is SEQ ID NO: 3.

Paragraph[8]. The variant of any of paragraphs 1-7, which has at least 75%, at least 80%, at least 85%, at least 90%, at least 95% identity, at least 96%, at least 97%, at least 98%, or at least 99%, but less than 100%, sequence identity to the amino acid sequence of the parent glucoamylase.

Paragraph[9]. The variant of any of paragraphs 1-8, which has at least 75%, at least 80%, at least 85%, at least 90%, at least 95%, at least 96%, at least 97%, at least 98%, or at least 99%, but less than 100% sequence identity to the polypeptide of SEQ ID NO: 3.

Paragraph[10]. The variant of any of paragraphs 1-9, wherein the number of substitutions is 1-20, e.g., 1-10 and 1-5, such as 1, 2, 3, 4, 5, 6, 7, 8, 9 or 10 substitutions.

Paragraph[11]. The variant of any of paragraphs 1-10, which comprises a substitution at a position corresponding to position 45.

Paragraph[12]. The variant of paragraph 11, wherein the substitution is with Lysine.

Paragraph[13]. The variant of any of paragraphs 1-10, which comprises a substitution at a position corresponding to position 46.

Paragraph[14]. The variant of paragraph 13, wherein the substitution is with Histidine.

Paragraph[15]. The variant of any of paragraphs 1-10, which comprises a substitution at a position corresponding to position 61.

Paragraph[16]. The variant of paragraph 15, wherein the substitution is with Threonine or Alanine.

Paragraph[17]. The variant of any of paragraphs 1-10, which comprises a substitution at a position corresponding to position 86.

Paragraph[18]. The variant of paragraph 17, wherein the substitution is with Cysteine.

Paragraph[19]. The variant of any of paragraphs 1-10, which comprises a substitution at a position corresponding to position 119.

Paragraph[20]. The variant of paragraph 19, wherein the substitution is with Tryptophan.

Paragraph[21]. The variant of any of paragraphs 1-10, which comprises a substitution at a position corresponding to position 120.

Paragraph[22]. The variant of paragraph 21, wherein the substitution is with Glycine.

Paragraph[23]. The variant of any of paragraphs 1-10, which comprises a substitution at a position corresponding to position 318.

Paragraph[24]. The variant of paragraph 23, wherein the substitution is with Tryptophan.

Paragraph[25]. The variant of any of paragraphs 1-10, which comprises a substitution at a position corresponding to position 348.

Paragraph[26]. The variant of paragraph 25, wherein the substitution is with Threonine.

Paragraph[27]. The variant of any of paragraphs 1-26, which comprises a substitution at two positions corresponding to any of positions 45, 46, 61, 86, 119, 120, 318 and 348.

Paragraph[28]. The variant of any of paragraphs 1-27, which comprises a substitution at three positions corresponding to any of positions 45, 46, 61, 86, 119, 120, 318 and 348.

Paragraph[29]. The variant of any of paragraphs 1-28, which comprises a substitution at four positions corresponding to any of positions 59, 95, 119, 121, 18, 426, and 316.

Paragraph[30]. The variant of any of paragraphs 1-29, which comprises a substitution at five positions corresponding to any of positions 45, 46, 61, 86, 119, 120, 318 and 348.

Paragraph[31]. The variant of any of paragraphs 1-30, which comprises a substitution at six positions corresponding to any of positions 45, 46, 61, 86, 119, 120, 318 and 348.

Paragraph[32]. The variant of any of paragraphs 1-31, which comprises a substitution at each position corresponding to positions 45, 46, 61, 86, 119, 120, 318 and 348.

Paragraph[33]. The variant according to paragraphs 1-32, wherein the variant comprises or consists of one or more substitutions selected from the group consisting of T45K, S46H, V61A, V61T, S86C, T119W, D120G, M318W, N348T and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3.

Paragraph[34]. The variant of any of the preceding paragraphs, wherein the variant comprises at least one of the following substitutions or combinations of substitutions:
T119W;
V61A;
D120G;
S86C+T119W;
T45K+T119W;
T119W+D120G;

T45K+D120G;
V61T+T119W;
D120G+M318W;
T45K+S46H;
T119W+D120G+N348T;
T119W+D120G+M318W;
S86C+T119W+D120G;
S46H+T119W+D120G;
T45K+T119W+D120G and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3.

Paragraph[35]. The variant according to paragraphs 1-34, which has an improved property relative to the parent, wherein the improved property is increased thermostability.

Paragraph[36]. A composition comprising the polypeptide of any of paragraphs 1-35.

Paragraph[37]. The composition according to paragraph 36, comprising an alpha-amylase and a polypeptide of any of paragraphs 1-35.

Paragraph[38]. The composition according to paragraph 36, comprising an alpha-amylase, an isoamylase and a polypeptide of any of paragraphs 1-35.

Paragraph[39]. The composition according to paragraph 36, comprising an pullulanase and a polypeptide of any of paragraphs 1-35.

Paragraph[40]. A use of a polypeptide of any of paragraphs 1-35 for production of syrup and/or a fermentation product.

Paragraph[41]. The use according to paragraph 40, wherein the starting material is gelatinized or un-gelatinized starch-containing material.

Paragraph[42]. A process of producing a fermentation product from starch-containing material comprising the steps of: (a) liquefying starch-containing material in the presence of an alpha amylase; (b) saccharifying the liquefied material; and (c) fermenting with a fermenting organism; wherein step (a) and/or step (b) is carried out using at least a glucoamylase variant of any of paragraphs 1-35.

Paragraph[43]. A process of producing a fermentation product from starch-containing material, comprising the steps of: (a) saccharifying starch-containing material at a temperature below the initial gelatinization temperature of said starch-containing material; and (b) fermenting with a fermenting organism, wherein step (a) is carried out using at least a glucoamylase variant of any of paragraphs 1-35.

Paragraph[44] A process of producing a syrup product from starch-containing material, comprising the step of: saccharifying starch-containing material at a temperature below the initial gelatinization temperature of said starch-containing material in the presence of a glucoamylase variant of any of paragraphs 1-40.

Paragraph[45]. A process of producing a syrup product from starch-containing material, comprising the step of: (a) liquefying starch-containing material in the presence of an alpha amylase; (b) saccharifying the liquefied material in the presence of a glucoamylase variant of any of paragraphs 1-40.

Paragraph[46] The process according to paragraph 45, wherein step b) further comprises adding a pullulanase.

Paragraph[47]. The process according to paragraphs 45 and 46, wherein the saccharification temperature is the range from 40 to 65° C., more particular from 50 to 62° C., more particular from 59 to 62° C.

Paragraph[48] An isolated polynucleotide encoding the variant of any of paragraphs 1-35.

Paragraph[49]. A nucleic acid construct comprising the polynucleotide of paragraph 42.

Paragraph[50]. An expression vector comprising the polynucleotide of paragraph 42.

Paragraph[51]. A host cell comprising the polynucleotide of paragraph 42.

Paragraph[52]. A method of producing a glucoamylase variant, comprising: cultivating the host cell of paragraph 51 under conditions suitable for expression of the variant; and recovering the variant glucoamylase.

The present invention is further described by the following examples that should not be construed as limiting the scope of the invention.

EXAMPLES

Materials and Methods
Glucoamylase Activity
Glucoamylase activity may be measured in AGU Units.
Glucoamylase Activity (AGU)

The Glucoamylase Unit (AGU) is defined as the amount of enzyme, which hydrolyses 1 micromole maltose per minute under the standard conditions (37° C., pH 4.3, substrate: maltose 100 mM, buffer: acetate 0.1 M, reaction time 6 minutes as set out in the glucoamylase incubation below), thereby generating glucose.

| glucoamylase incubation: | |
| --- | --- |
| Substrate: | maltose 100 mM |
| Buffer: | acetate 0.1M |
| pH: | 4.30 ± 0.05 |
| Incubation temperature: | 37° C. ± 1 |
| Reaction time: | 6 minutes |
| Enzyme working range: | 0.5-4.0 AGU/mL |

The analysis principle is described by 3 reaction steps:
Step 1 is an enzyme reaction:
Glucoamylase (AMG), EC 3.2.1.3 (exo-alpha-1,4-glucan-glucohydrolase), hydrolyzes maltose to form alpha-D-glucose. After incubation, the reaction is stopped with NaOH.
Steps 2 and 3 result in an endpoint reaction:
Glucose is phosphorylated by ATP, in a reaction catalyzed by hexokinase. The glucose-6-phosphate formed is oxidized to 6-phosphogluconate by glucose-6-phosphate dehydrogenase. In this same reaction, an equimolar amount of NAD+ is reduced to NADH with a resulting increase in absorbance at 340 nm. An autoanalyzer system such as Konelab 30 Analyzer (Thermo Fisher Scientific) may be used.

| Color reaction | |
| --- | --- |
| Tris | approx. 35 mM |
| ATP | 0.7 mM |
| NAD$^+$ | 0.7 mM |
| Mg$^{2+}$ | 1.8 mM |
| Hexokinase | >850 U/L |
| Glucose-6-P-DH | >850 U/L |
| pH | approx. 7.8 |
| Temperature | 37.0° C. ± 1.0 ° C. |
| Reaction time | 420 sec |
| Wavelength | 340 nm |

Purification of Site-directed Tc AMG Variants
The protein purification was carried out by affinity chromatography using α-cyclodextrin. A-cyclodextrin acts as a substrate analogue for Tc-AMG (*Trametes cingulata* AMG), the enzyme does not degrade the compound and can be eluted using α-cyclodextrin in the elution buffer.

Preparation of Purification Matrix

Materials
- Alfa-cyclodextrin (Fluka 28705)
- DVs agarose activated with di-vinyl sulfone (Mini leak high Kem-en-Tec 1013F)
- Coupling buffer; K2HPO4 (0.5M, pH 11)
- Wash buffer; Phosphate buffer (0.5M, pH 7)
- Blocking buffer; Ethanolamine (0.1 M) (E9508)

Procedure

Wash the matrix (50 ml) with 5×100 ml milliQ water, on suction filter (sintered glass, G4). α-cyclodextrin (6 g) was dissolved in coupling buffer (100 ml). The suck dried matrix was transferred to the α-cyclodextrin solution and rotated overnight. The coupled matrix was washed with wash buffer (5×100 ml). The matrix was blocked with blocking buffer for 2 hours with rotation. The matrix was washed with ultra pure water (5×100 ml), on suction filter (sintered glass, G4). The coupled matrix was stored in ethanol (20%) for future use.

Filtration

The *Aspergillus* fermentation was filtered first through a sandwich of glass fibre filters (GF/A, C, F, in the order from the top) and then sterile filtered through 0.2μ filter using a tangential flow filter cartridge fixed to GE QuixStand.

Purification
- Matrix: Alfa-cyclodextrin (20 ml)
- Equilibration buffer (A buffer): 50 mM Na-Acetate pH 4,5
- B buffer: 50 mM Na-Acetate, 1% alfa-CD (fluka28705) pH 4,5
- Elution: isocratic in elution buffer (5% B and 95% A)
- Flow rate 8 ml/min
- Fraction collection size 14 ml
- The matrix was packed in a glass column and equilibrated with the equilibration buffer (200 ml)
- The filtered fermentation broth (sample) was passed through the column
- The post sample wash was performed by passing equilibration buffer (200 ml).
- The protein was eluted by passing elution buffer (200 ml)
- The fractions (14 ml) which had absorbance at 280 was pooled.
- This pool was designated as the purified sample.

Glucoamylase Stability Assay—Residual Activity (Cultured Supernatant)

Reagents:
1. Culture supernatant sample: 10× dilution were made for the culture supernatant using 100 mM Acetate buffer pH 4.5
2. Stock Solution of 1M Acetate Buffer pH 4.5 (500 ml)
   a. Sodium acetate (Sigma S7546 Batch No. 125K0085): (41.015 g)
   b. pH adjusted with acetic acid
   c. Volume made up to 500 ml using Type I water
   Stored at 4° C.
3. 0.1M Borax (Sodium Tetraborate) solution (500 ml)
   a. Di-Sodium tetraborate decahydrate: (19.068 g)
   b. Dissolved in Type I water and volume made up to 500 ml
   Stored at Room temperature
4. p-Nitrophenyl-α-D-glucopyranoside (pNPG) Substrate: 0.2% (6.66 mM)
   a. 200 mg of pNPG
   b. 10 ml of 1M Acetate Buffer pH 4.5
   c. Type I water up to 100 ml Stored at 4° C. after preparation till use (should be prepared freshly every day for assay)

5. Standard Solution
   a. Tc-AMG WT Purified sample is used as standard in the assay
   b. Concentration of the enzyme is 0, 2, 4, 6, 8, 12, 16 and 20 μg/ml was prepared and 90 μl of this is taken in the assay Procedure 90 μl of diluted culture supernatant was taken in PCR plates in triplicates and standard solution is pipetted into the plate with one plate will be control. One set was kept at 4° C. as control. Second set was subjected to stress at 60° C. for 20 min one plate at a time using Thermal cycler. Immediately after stress cooled to 4° C. and stored in refrigerator till assay. To the stressed plate 90 ul of standard solution is pipette and stored at 4° C. till the time of assay.

Enzyme Assay

One PCR Plate either 4° C. control or stressed sample are taken which contains 90 μl of samples and kept in the thermal cycler which is at 4° C. 30 μl of 0.2% pNPG substrate solution is added to the enzyme and incubated at 40° C. for 30 min. Reaction is stopped using 120 μl of 0.1M Sodium tetraborate solution. Similarly the second set for control, 2 plates of stressed sample is assayed as mentioned above and followed by stressed samples in the same way. From this 120 μl of the sample is transferred to 96 Well MTP Plate and absorbance measured at 405 nm.

Glucoamylase Stability Assay—Residual Activity (Purified Sample)

Reagents:
1. Purified protein sample:—Normalized to 10 μg/ml
2. Stock Solution of 1M Acetate Buffer pH 4.5 (500 ml)
   Sodium acetate (Sigma S7546 Batch No. 125K0085): (41.015 g)
   pH adjusted with acetic acid
   Volume made up to 500 ml using Type I water
   Stored at 4° C.
3. 0.1 M Borax (Sodium Tetraborate) solution (500 ml)
   Di-Sodium tetraborate decahydrate: (19.068 g)
   Dissolved in Type I water and volume made up to 500 ml
   Stored at Room Temperature
4. pNPG Substrate: 0.2% (6.66 mM)
   200 mg of pNPG
   10 ml of 1M Acetate Buffer pH 4.5
   Type 1 water up to 100 ml
   Stored at 4° C. after preparation till use (should be prepared freshly every day for assay)
5. Standard solution
   TcAMG WT Purified sample is used as standard in the assay
   Concentration of the enzyme is 0, 2, 4, 6, 8, 12, 16 and 20 μg/ml was prepared and 90 μl of this is taken in the assay Procedure 90 μl of diluted enzyme sample is taken in PCR plates in triplicates, and standard solution is also pipette into the plate for one plate which will be control. One set was kept at 4° C. as control. Second set was subjected to stress at 60° C. for 20 min one plate at a time using Thermal cycler. Immediately after stress cooled to 4° C. and stored in refrigerator till assay. To the stressed plate 90 μl of standard solution is pipette and stored at 4° C. till the time of assay.

Enzyme Assay

One PCR Plate either 4° C. control or stressed sample are taken which contains 90 μl of samples and kept in the thermal cycler at 4° C. 30 μl of 0.2% pNPG substrate solution is added to the enzyme and incubated at 40° C. for 30 min. Reaction is stopped using 120 μl of 0.1M Sodium tetraborate solution. Similarly the second set which contains plates of stressed sample is assayed as mentioned above and followed by stressed samples in the same way. From this 120 µl of the sample is transferred to 96 Well MTP Plate and absorbance measured at 405 nm.

Thermostability Analysis by Differential Scanning Calorimitry (DSC)

The improved variants selected from the residual activity assay were also tested using Differential Scanning calorimitry as described by Freire, E. (1995) (Methods. Mol. Biol. 41, 191-218).

The thermo-stability of the purified Tc-AMG derived variants were determined at pH 4.5 (50 mM Sodium Acetate) by Differential Scanning calorimetry (DSC) using a VP-Capillary Differential Scanning calorimeter (MicroCal Inc., Piscataway, N.J., USA). The thermal denaturation temperature, Td (° C.), was taken as the top of the denaturation peak (major endothermic peak) in thermograms (Cp vs. T) obtained after heating enzyme solutions in selected buffers (50 mM Sodium Acetate, pH 4.5) at a constant programmed heating rate of 200 K/hr.

Sample- and reference-solutions (approximately 0.3 ml of 0.4 mg/ml) were loaded into the calorimeter (reference: buffer without enzyme) from storage conditions at 10° C. and thermally pre-equilibrated for 10 minutes at 20° C. prior to DSC scan from 20° C. to 110° C. Denaturation temperatures were determined with an accuracy of approximately +/−1° C.

Example 1

Cloning and Expression of the Glucoamylase (AMG) Gene from *Trametes cingulate*

An expression construct, pHUda440, containing the wild type *T. cingulata* AMG was described in WO2006/069289 in Example 4. This construct comprises the polynucleotide sequence shown herein as SEQ ID NO: 1 and encoding the mature polypeptide shown herein as amino acids 18 to 576 of SEQ ID NO: 2 corresponding to SEQ ID NO: 3. WO2006/069289 further describes the expression of wild type *T. cingulata* AMG from pHUda440.

Example 2

Variant Generation by Site-directed Mutagenesis

Based on the plasmid disclosed in WO2006/069289 expressing the wild type *T. cingulata* AMG, each of the specific site directed mutations as disclosed herein can be generated by designing the appropriate primers. The resulting genes can be cloned and expressed by methods known to the skilled person.

The specific variants constructed and tested for improved thermo-stability disclosed in the below table.

Example 3

Improved Thermo-stability of Specific Single Substitutions Measured by DSC and Residual Glucoamylase Activity Primary screening was carried out using culture supernatant samples and measuring residual activity using the glucoamylase thermal stability assay described above. This initial analysis identified improved thermo-stable variants compared to the wild type. The improved variants were selected based on the assay results. The Assay reaction was carried out in 100 mM Sodium acetate buffer pH 4.5. The reaction mixture consists of 90 ul of 10 times (Buffer 100 mM Acetate buffer pH 4.5) diluted culture supernatant and stressed at 60° C. for 20 min and to the same sample 30 µl of the substrate (0.2% in buffer). Samples were incubated at 40° C. for 30 min and the reaction was stopped by adding 120 µl of sodium tetraborate and the absorbance measured at 405 nm. Similarly control reactions were done which had not been subjected to thermal stress. The control activity was considered as 100% and the residual activity was calculated relative to the control. The selected variants should have improved thermo-stability over the wt glucoamylase. The improved variants are listed below in the table.

TABLE 1

Residual activity and DSC data of single substituted variants

| Mutation | % Residual Activity | Td (Deg C) |
| --- | --- | --- |
| T45K | 67 | 77.2 |
| V61A | 68 | 74.6 |
| S46H | 75 | 76.6 |
| V61T | 78 | 75.9 |
| S86C | 86 | 75.4 |
| T119W | 80 | 76.7 |
| D120G | 86 | 78.5 |
| M318W | 79 | 76.0 |
| N348T | 80 | 75.3 |
| Wild Type | 65 | 75.3 |

Example 4

Improved Thermo-stability of Specific Combinations of Substitutions Measured by DSC and Residual Glucoamylase Activity Some of improved variants were chosen for making specific combinations of double or triple substitutions. The specific combinations were tested by measuring residual glucoamylase activity and thermal melting temperature by DSC.

The improved variants are listed below in the table 2

TABLE 2

Residual activity and DSC of combination of substituted variants

| Mutation | % Residual Activity | Td (Deg C) |
| --- | --- | --- |
| S86C + T119W | 75 | 77.3 |
| T45K + T119W | 84 | 78.3 |
| T119W + D120G | 96 | 79.6 |
| T45K + D120G | 94 | 79.0 |
| V61T + T119W | 74 | 77.3 |
| D120G + M318W | 84 | 77.7 |
| T45K + S46H | 77 | 77.0 |
| T119W + D120G + N348T | 82 | 78.0 |
| T119W + D120G + M318W | 85 | 79.4 |
| S46H + T119W + D120G | 86 | 79.6 |
| T45K + T119W + D120G | 60 | 80.4 |
| Wild Type | 60 | 75.2 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A glucoamylase variant comprising a substitution at one or more positions corresponding to positions 45, 46, 61, 86, 119, 120, 318, 348 of the polypeptide of SEQ ID NO: 3 wherein the variant has glucoamylase activity and wherein the variant has at least 80%, but less than 100% sequence identity to the polypeptide of SEQ ID NO: 3.

2. The variant according to claim 1, wherein the number of substitutions is 1-20.

3. The variant of claim 1, wherein the variant comprises or consists of one or more substitutions selected from the group consisting of T45K, S46H, V61A, V61T, S86C, T119W, D120G, M318W, N348T and wherein the variant has glucoamylase activity and wherein the variant has at least 80%, but less than 100% sequence identity to the polypeptide of SEQ ID NO: 3.

4. The variant of claim 1, wherein the variant comprises at least one of the following substitutions or combinations of substitutions:
T119W;
V61A;
D120G;
S86C+T119W;
T45K+T119W;
T119W+D120G;
T45K+D120G;
V61T+T119W;
D120G+M318W;

T45K+S46H;
T119W +D120G+N348T;
T119W+D120G+M318W;
S86C+T119W+D120G;
S46H+T119W+D120G;
T45K+T119W+D120G and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3.

5. The variant of claim 1, which has an improved property relative to the parent, wherein the improved property is increased thermostability.

6. A composition comprising the polypeptide of claim 1.

7. The composition according to claim 6, comprising an alpha-amylase and a polypeptide of claim 1.

8. A process of producing a fermentation product from starch-containing material comprising the steps of: (a) liquefying starch-containing material in the presence of an alpha amylase; (b) saccharifying the liquefied material; and (c) fermenting with a fermenting organism; wherein step (a) and/or step (b) is carried out using at least a glucoamylase variant of claim 1.

9. A process of producing a syrup product from starch-containing material, comprising the step of: (a) liquefying starch-containing material in the presence of an alpha amylase; (b) saccharifying the liquefied material in the presence of a variant glucoamylase of claim 1.

10. An isolated polynucleotide encoding the variant of claim 1.

11. A nucleic acid construct comprising the polynucleotide of claim 10.

12. An expression vector comprising the polynucleotide of claim 10.

13. A host cell comprising the polynucleotide of claim 10.

14. A method of producing a glucoamylase variant, comprising: cultivating the host cell of claim 13 under conditions suitable for expression of the variant; and recovering the variant glucoamylase.

15. The variant of claim 1, having at least at least 85% sequence identity to the polypeptide of SEQ ID NO: 3.

16. The variant of claim 1, having at least at least 90% sequence identity to the polypeptide of SEQ ID NO: 3.

17. The variant of claim 1, having at least at least 95% sequence identity to the polypeptide of SEQ ID NO: 3.

18. The variant of claim 1, having at least at least 97% sequence identity to the polypeptide of SEQ ID NO: 3.

19. The variant of claim 1, having at least at least 98% sequence identity to the polypeptide of SEQ ID NO: 3.

20. The variant of claim 1, having at least at least 99% sequence identity to the polypeptide of SEQ ID NO: 3.

* * * * *